United States Patent
Zhang

(10) Patent No.: US 8,560,069 B2
(45) Date of Patent: Oct. 15, 2013

(54) SYSTEM FOR CARDIAC ARRHYTHMIA DETECTION

(75) Inventor: Hongxuan Zhang, Palatine, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 393 days.

(21) Appl. No.: 12/871,071

(22) Filed: Aug. 30, 2010

(65) Prior Publication Data

US 2011/0166618 A1   Jul. 7, 2011

Related U.S. Application Data

(60) Provisional application No. 61/292,285, filed on Jan. 5, 2010.

(51) Int. Cl.
*A61N 1/37* (2006.01)

(52) U.S. Cl.
USPC ............................................. 607/28

(58) Field of Classification Search
USPC ....................................... 607/4–28
See application file for complete search history.

(56) References Cited

U.S. PATENT DOCUMENTS

| | | | |
|---|---|---|---|
| 5,718,235 A | 2/1998 | Golosarsky et al. | |
| 5,755,737 A | 5/1998 | Prieve et al. | |
| 5,846,263 A | 12/1998 | Peterson et al. | |
| 5,931,857 A | 8/1999 | Prieve et al. | |
| 6,625,489 B2 | 9/2003 | Sheth et al. | |
| 6,708,062 B2 | 3/2004 | Ericksen et al. | |
| 6,731,979 B2 | 5/2004 | MacDonald | |
| 6,845,268 B2 | 1/2005 | Hill et al. | |
| 7,039,461 B1 | 5/2006 | Lovett | |
| 7,062,325 B1 | 6/2006 | Krig et al. | |
| 7,133,720 B2 | 11/2006 | Seim | |
| 7,149,576 B1 | 12/2006 | Baura et al. | |
| 7,181,278 B2 | 2/2007 | Kramer et al. | |
| 7,212,860 B2 | 5/2007 | Stahmann et al. | |
| 7,239,914 B2 | 7/2007 | Lovett et al. | |
| 7,248,921 B2 | 7/2007 | Palreddy et al. | |
| 7,280,869 B2 | 10/2007 | Warman et al. | |
| 7,383,086 B2 * | 6/2008 | Ding | 607/9 |
| 7,532,929 B2 | 5/2009 | Mussig et al. | |
| 7,532,930 B2 * | 5/2009 | Schermeier et al. | 607/28 |
| 7,542,794 B1 | 6/2009 | Zhang et al. | |
| 7,546,160 B2 | 6/2009 | Stahmann et al. | |
| 7,561,913 B2 | 7/2009 | Mongeon et al. | |
| 7,590,448 B2 | 9/2009 | De Vries | |
| 8,126,552 B2 * | 2/2012 | Min | 607/17 |
| 2004/0193223 A1 * | 9/2004 | Kramer et al. | 607/9 |
| 2009/0259266 A1 * | 10/2009 | Zhang et al. | 607/3 |

* cited by examiner

*Primary Examiner* — Rex R Holmes
(74) *Attorney, Agent, or Firm* — Peter R. Withstandley

(57) ABSTRACT

A system for heart performance characterization and abnormality detection includes an interface for receiving sampled data representing an electrical signal indicating electrical activity of a patient heart over multiple heart beat cycles and for receiving a pace signal indicating occurrence of a heart pace pulse applied to the heart. A signal processor uses the received sampled data and pace signal in calculating, a first signal characteristic value comprising a time interval between occurrence of the pace pulse and a cardiac cycle characteristic and a second signal characteristic comprising an average of the time intervals determined over a multiple heart cycles. A comparator compares at least one of the first and second characteristic values with a threshold value to provide a comparison indicator. A patient monitor generates an alert message associated with the threshold in response to the comparison indicator indicating a calculated signal characteristic value exceeds the threshold value.

20 Claims, 7 Drawing Sheets

| Synchronized time duration | Calculation and analysis | Diagnosis and detection |
|---|---|---|
| Pace_Q | 1. Pace_Q time (mS) and averaging time (mean): $\mu(Pace\_Q)$<br>2. Pace Q standard deviation: $\phi(Pace\_Q)$<br>3. Signal Variability = $\dfrac{\mu(Pace\_Q)}{\phi(Pace\_Q)}$<br>4. Signal Variation= $\dfrac{\max(Pace\_Q - \mu(Pace\_Q))}{\mu(Pace\_Q)}$ | Starting time of the depolarization detection can help to track the time pacing stimulation timing variation associated with a ventricle. |
| Pace_R | 1. Pace_R time (mS) and averaging time (mean): $\mu(Pace\_R)$<br>2. Pace R standard deviation: $\phi(Pace\_R)$<br>3. Signal Variability = $\dfrac{\mu(Pace\_R)}{\phi(Pace\_R)}$<br>4. Signal Variation= $\dfrac{\max(Pace\_R - \mu(Pace\_R))}{\mu(Pace\_R)}$ | R wave is the center of the depolarization procedure. R wave latency from Pacing spike is an indication of the depolarization. (Prolonged R wave latency indicates excitation pathway blockage or serious heart disease.) |
| Pace_S | 1. Pace_S time (mS) and averaging time (mean): $\mu(Pace\_S)$<br>2. Pace S standard deviation: $\phi(Pace\_S)$<br>3. Signal Variability = $\dfrac{\mu(Pace\_S)}{\phi(Pace\_S)}$<br>4. Signal Variation= $\dfrac{\max(Pace\_S - \mu(Pace\_S))}{\mu(Pace\_S)}$ | S wave is the end of depolarization and start of repolarization. S wave latency indicates healthy switching between the two procedures. |
| Pace_T | 1. Pace_T time (mS) and averaging time (mean): $\mu(Pace\_T)$<br>2. Pace T standard deviation: $\phi(Pace\_T)$<br>3. Signal Variability = $\dfrac{\mu(Pace\_T)}{\phi(Pace\_T)}$<br>4. Signal Variation= $\dfrac{\max(Pace\_T - \mu(Pace\_T))}{\mu(Pace\_T)}$ | T wave is a later potential (voltage) parameter of cardiac electrophysiological activities. T wave latency can be used to track the abnormal changes of the ventricle, such as myocardial ischemia. |

SYSTEM FOR CARDIAC ARRHYTHMIA DETECTION

This is a non-provisional application of provisional application Ser. No. 61/292,285 filed 5 Jan. 2010, by H. Zhang.

FIELD OF THE INVENTION

This invention concerns a system for heart performance characterization and abnormality detection by determining characteristics of an electrical signal indicating electrical activity of a patient heart over multiple heart beat cycles and a pace signal indicating occurrence of a heart pace pulse applied to the heart.

BACKGROUND OF THE INVENTION

Cardiac pacing is used for clinical treatment and therapy of a patient and involves electrical cardiac stimulation to treat a tachyarrhythmia or bradyarrythmia. The pacing re-establishes circulatory integrity and normal hemodynamics that are compromised by a slow or fast heart rate by restoring an appropriate heart rate. Cardiac pacing may be lifesaving. Cardiac response signal analyses based on electrophysiological activity (such as surface ECG signals and ICEG (intra-cardiac electrograms)) and time domain parameters of the waveforms are utilized for cardiac arrhythmia detection and diagnosis, such as of P wave associated disorders like atrial fibrillation (AF) and ST segment changes for myocardial ischemia and infarction. However during heart pacing or stimulation, the cardiac electrophysiology responses (such as signal morphology, latency) are different from cases in a non-pacing situation. Known systems using P wave analysis methods, for example, typically fail to efficiently interpret and characterize cardiac signals during pacing. Furthermore, noise and artifact effects during pacing may be higher which may distort a cardiac electrophysiological signal, resulting in a false positive alarm, especially in ICD (implantable cardioverter-defibrillator) patients.

Early cardiac arrhythmia and pathology recognition, such as of atrial fibrillation, myocardial ischemia or infarction, and ventricle tachycardia, is desirable for rhythm management of cardiac disorders and irregularities. Known waveform morphologies and time domain parameter analysis of depolarization and repolarization functions, such as of a P wave, QRS complex, ST segment, T wave, are used for cardiac arrhythmia monitoring and identification. Known systems typically use RR wave detection to synchronize signal interpretation beat to beat. However RR wave detection may not be accurate during pacing or during electrical stimulation, especially for excitation time tracking and detection of signal morphology variation. Additionally unsuccessful pacing heart beats may cause variation (as well as unnecessary alarms or warnings) in signal evaluation and calculation. Furthermore, there may be substantial heart electrophysiological characteristic changes: such as absence of a P wave in the pacing signals and detection of an ST segment exceeding a 0.1 mV threshold (as typically used for cardiac condition detection) may not work for ischemia detection in pacing (especially for intra-cardiac electrograms (ICEG)). Also substantial signal magnitude shift, distortion or variation may occur in the presence of pacing.

Further known clinical methods for cardiac arrhythmia identification and analysis based on ECG signals are subjective and need extensive expertise and clinical experience for accurate interpretation and appropriate cardiac rhythm management. Improved objective analysis and diagnosis of cardiac signals and activities is desirable. Known methods based on RR wave detection may indicate unnecessary time variation for cardiac signal morphology analysis and therefore may be inaccurate in cardiac function evaluation and pathology diagnosis and known methods based on detecting amplitude (voltage) changes and variation may not be accurate for cardiac function evaluation and pathology diagnosis. Known pacing cardiac signals analysis is typically subjective and needs extensive physician pacing analysis experience and may be not be able to qualitatively and quantitatively capture or characterize signal changes, and predict a pathological trend, especially a real time growing trend of a cardiac arrhythmia, such as a pathology trend from low risk to medium, and then to high risk (severe and fatal) rhythm (especially in VT growing arrhythmia, for example).

Known excitation analysis typically involves tune stamping an R wave transition along myocardial tissue (such as by using different leads in a catheter coupled to different portions of cardiac tissue) but lack accurate methods to measure time duration and variation of signals from individual cardiac tissue portions. Absolute time synchronization variation may be used to detect local malfunctioning cardiac tissue, such as from a pacing spike to R wave, pacing spike to Q or S wave, but this may not work when patient pacing occurs. In known clinical applications, pacing energy and rate determination are typically physician controlled based on experience and therefore prone to human error. A system according to invention principles addresses these deficiencies and related problems.

SUMMARY OF THE INVENTION

A system improves analysis and interpretation of cardiac electrophysiological activities, by characterizing cardiac electrophysiological signals (including surface ECG signals and intra-cardiac electrograms) by determining synchronization and statistical variation of different portions of a cardiac signal in response to synchronization with a pacing or stimulation signal. A system for heart performance characterization and abnormality detection includes an interface for receiving sampled data representing an electrical signal indicating electrical activity of a patient heart over multiple heart beat cycles and for receiving a pace signal indicating occurrence of a heart pace pulse applied to the heart. A signal processor uses the received sampled data and pace signal in calculating, a first signal characteristic value comprising a time interval between occurrence of the pace pulse and a cardiac cycle characteristic and a second signal characteristic comprising an average of the time intervals determined over a multiple heart cycles. A comparator compares at least one of the first and second characteristic values with a threshold value to provide a comparison indicator. A patient monitor generates an alert message associated with the threshold in response to the comparison indicator indicating a calculated signal characteristic value exceeds the threshold value.

BRIEF DESCRIPTION OF THE DRAWING

FIG. 3 shows a table summarizing functions for determining synchronized duration (latency) and variability characteristics for cardiac pathology and arrhythmia detection, according to invention principles.

DETAILED DESCRIPTION OF THE INVENTION

Figure 1:
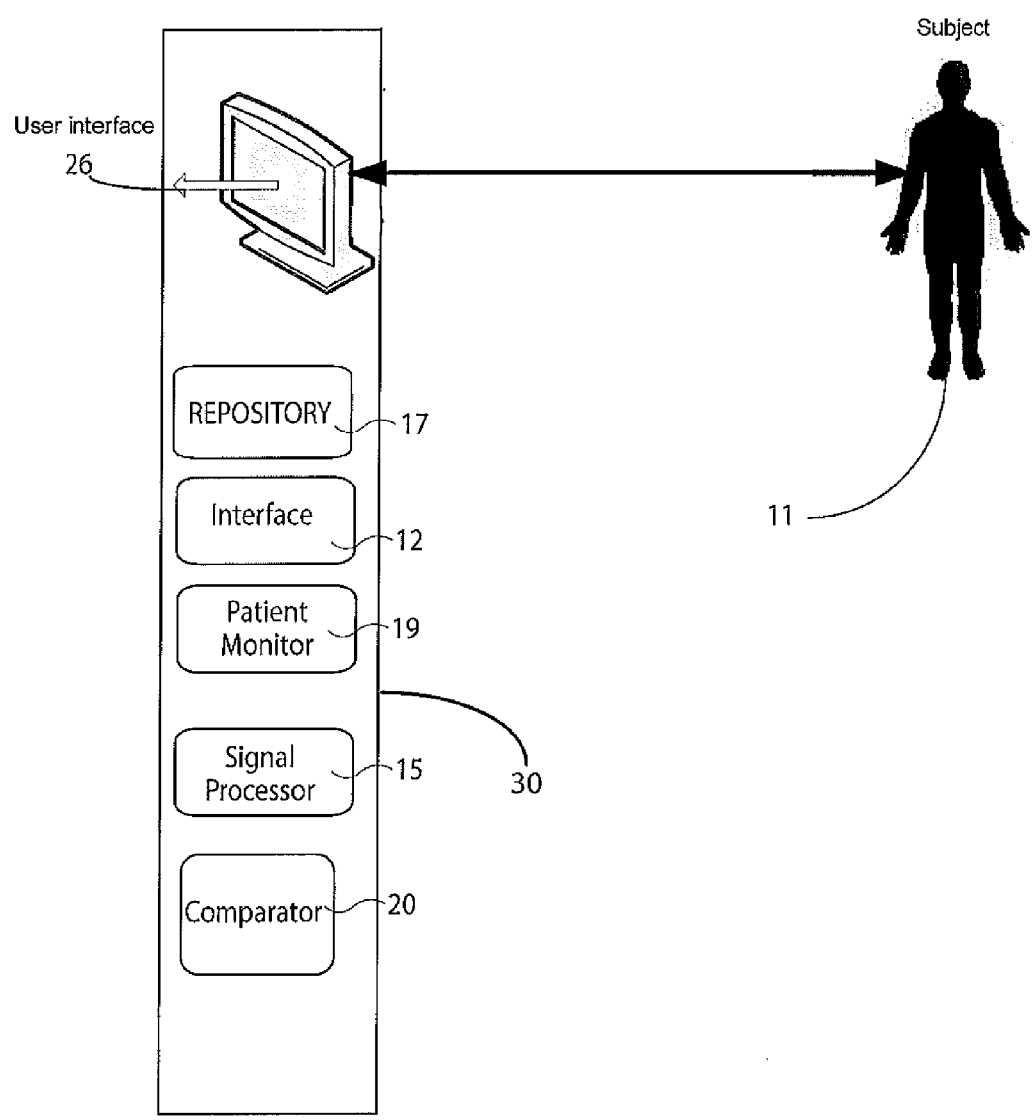
FIG. 1 shows a system for heart performance characterization and abnormality detection, according to invention principles.

A system improves accuracy and reliability of analysis and interpretation of cardiac electrophysiological activities, by characterizing cardiac electrophysiological signals (including surface ECG signals and intra-cardiac electrograms) in response to synchronization with a cardiac signal (such as for pacing or stimulation). The system synchronizes to locate and determine statistical characteristics and variation of different portions of a cardiac signal to provide an accurate time, location and severity of cardiac pathology and events for improved diagnosis. The system identifies cardiac disorders, differentiates cardiac arrhythmias, characterizes pathological severity, predicts life-threatening events, and supports evaluating drug delivery effects. The system analyzes cardiac electrophysiological signals and determines patient health status during pacing using pacing signal synchronization and stimulator control and adjustment (such as anti-tachycardia pacing) to provide an optimum pacing time, energy and rate for a pacing signal. The system performs mapping of synchronized multi-channel pacing signal characteristics to medical conditions for arrhythmia detection.

Pacing and stimulation employ external stimulation (such as a pacing signal from an intra-coronary device, pacemaker or external stimulator) to replace a heart impulse which would normally be generated by a sino atrial node. When a heart is controlled using pacing impulses, the heart electrophysiological activities and excitation transition are synchronized. The heart electrophysiological signals still show a QRS complex and T wave. However, clinical information is buried in pacing cardiac signals and is not fully extracted for cardiac pathology and event analysis using known systems. In contrast, the system objectively analyzes cardiac data and reduces need for extensive clinical experience and knowledge. The system provides cardiac signal amplitude (voltage) analysis and a health indicator as well as analysis of time duration and synchronization signal latency under pacing and stimulation. The system further performs variability analysis of time duration between pacing spikes to an X wave portion (representing a cardiac signal portion, such as R wave, T wave) and extracts early information concerning cardiac pathology and events which facilitates early cardiac impairment detection.

Pacing signal based synchronized cardiac tissue activity and electrophysiological response data are used for controlling and adjusting stimulation and pacing parameters, such as delivered current, pacing pulse width and pacing rate. This reduces electrical shock risk to patient heart tissue and noise in EP (electrophysiological) signal recording and monitoring. The system in one embodiment is implemented to provide automatic pacing and stimulation, such as in ICD patients. The system further provides multi-beat averaging for cardiac signal analysis with a high signal to noise ratio by pacing and stimulation spike synchronization. This improves signal diagnosis sensitivity and stability of cardiac arrhythmia detection. The system maps parameters derived from multi-channel synchronized signals acquired from different intra-cardiac sites (accommodating latency from a pacing spike) to corresponding medical conditions using predetermined mapping information for real time 3D heart function and pathology monitoring and detection.

FIG. 1 shows system 10 for heart performance characterization and abnormality detection. System 10 analyzes electrophysiological signals (including surface ECG, intra-cardiac electrograms, and heart activity signals, such as a cardiac sound waveform) by determining synchronization and statistical variation of different portions of a cardiac signal in response to synchronization with a pacing or stimulation signal. System 10 comprises at least one computer system, workstation, server or other processing device 30 including interface 12, repository 17, patient monitor 19, signal processor 15, comparator 20 and a user interface 26. Interface 12 receives sampled data representing an electrical signal indicating electrical activity of a patient heart over multiple heart beat cycles and receives a pace signal indicating occurrence of a heart pace pulse applied to the heart. Signal processor 15 uses the received sampled data and pace signal in calculating, a first signal characteristic value comprising a time interval between occurrence of the pace pulse and a cardiac cycle characteristic and a second signal characteristic comprising an average of the time intervals determined over multiple heart cycles. Comparator 20 compares at least one of the first and second characteristic values with a threshold value to provide a comparison indicator. Patient monitor 19, in response to the comparison indicator indicating the calculated signal characteristic value exceeds the threshold value, generates an alert message associated with the threshold.

Figure 2:
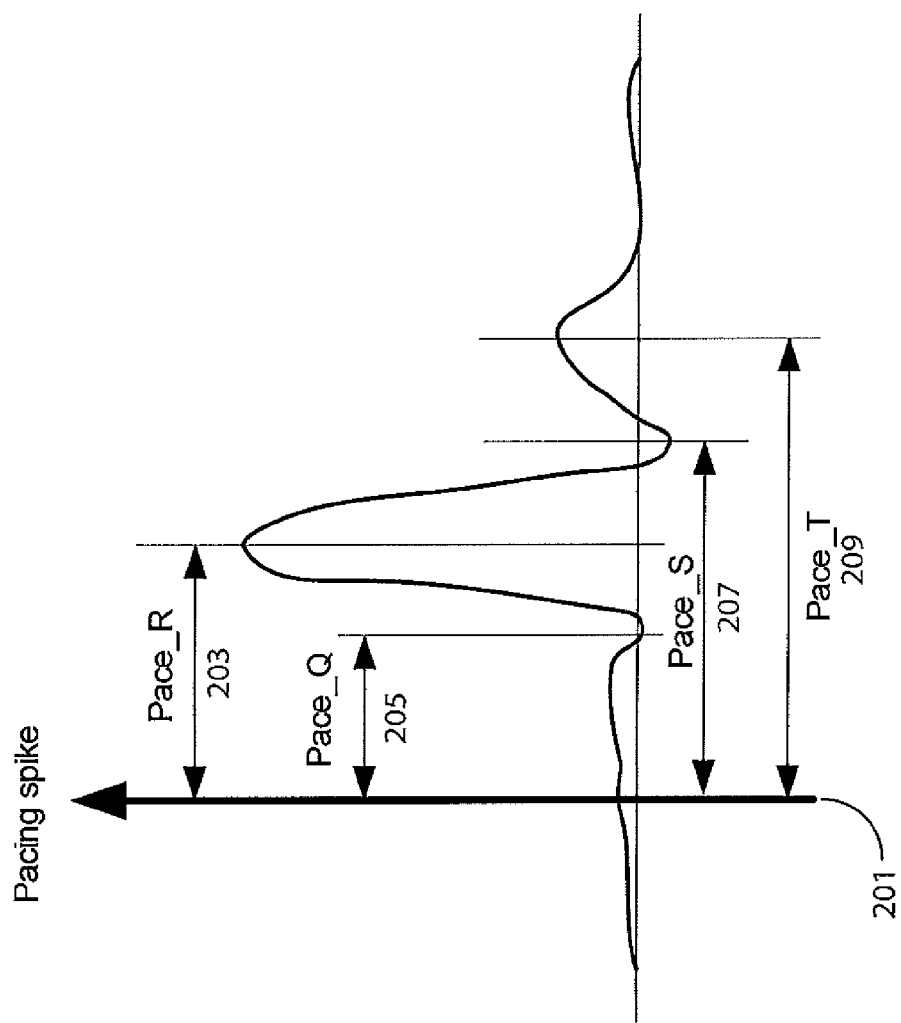
FIG. 2 illustrates waveform characteristics of a paced heart beat, according to invention principles.

FIG. 2 illustrates waveform characteristics of a paced heart beat. The term Pace_X as used herein represents a time duration between a pacing electrical spike to an X wave (such as Q wave, R wave). For example, Pace_R 203 means the time from a pacing spike to an R wave, which indicate the time duration of the heart contraction and squeezing response time. The time duration variation (synchronized with a pacing spike) is utilized for detecting and diagnosing cardiac tissue pathologies and function distortions. System 10 advantageously generates pacing related signal parameters for use in diagnosis and characterization of cardiac health and arrhythmias. FIG. 2 shows a typical pacing heart beat with pacing spike 201. System 10 measures the heart electrophysiological activity and response (including Q wave 205, R wave 203, S wave 207, T wave 209, representing depolarization and repolarization activity) relative to pacing synchronized signal 201.

FIG. 3 shows a table summarizing functions for determining synchronized duration (latency) and variability characteristics for cardiac pathology and arrhythmia detection. The calculated functions are performed for a specific interesting portion of a heart cycle, such as a U wave. Column 333 identifies the functions calculated for Pace_Q 310, Pace_R 320, Pace_S 322 and Pace_T 324 (column 330) time durations, respectively. Specifically, the functions calculated include Mean or averaging value (expectation);

$$\mu(\text{Pace\_X}) = \frac{1}{N}\sum_{i \in N} \text{Pace\_X}(i);$$

Standard deviation:

$$\phi(\text{Pace\_X}) = \frac{1}{N-1} \sum_{i \in N-1} (\text{Pace\_X}(i) - \mu(\text{Pace\_X}))$$

$$\text{Signal Variability} = \frac{\mu(\text{Pace\_X})}{\phi(\text{Pace\_X})} \text{ and}$$

$$\text{Signal Variation} = \frac{\max(\text{Pace\_X} - \mu(\text{Pace\_X}))}{\mu(\text{Pace\_X})},$$

for each of Pace_Q 310, Pace_R 320, Pace_S 322 and Pace_T 324, where Pace_X is the time duration from pacing spike to X wave (such as Q wave, R wave); N is a calculation window size (there are N heart beat in a shifting calculation window).

Column 336 identifies the anatomical features and medical conditions associated with the Pace_Q 310, Pace_R 320, Pace_S 322 and Pace_T 324 calculated parameters. Specifically, the calculated parameters concerning the Pace_Q 310 time duration indicate characteristics of start time of depolarization detection and track pacing stimulation timing variation associated with a ventricle. The calculated parameters concerning the Pace_R 320 time duration indicate characteristics of R wave latency from a Pacing spike and reveal depolarization behavior. Prolonged R wave latency indicates excitation pathway blockage or serious heart disease, for example, since an R wave is the center of the depolarization procedure. The calculated parameters concerning the Pace_S 322 time duration indicate characteristics of S wave latency and switching between depolarization and repolarization procedures since an S wave is the end of depolarization and start of repolarization. The calculated parameters concerning the Pace_T 324 time duration indicate characteristics of T wave latency used to detect and track abnormal changes of a ventricle, such as myocardial ischemia since a T wave is a later potential (voltage) parameter of cardiac electrophysiological activities.

Pacing or stimulation is used to facilitate advance of normal contraction of a patient heart at a given pace. A pacing signal is also used to induce a different pacing rate to test and verify if heart tissue can catch up with an excitation signal and work normally for use in AF treatment and verification, for example. A 10% higher heart rate compared to a patient normal heart rate is typically used for this purpose. However, not every pacing signal can generate a successful heart beat cycle and drive heart tissue in healthy squeezing operation. A compound beat or an unsuccessful pacing conduction beat, for example, may result from pacing problems and patient cardiac diseases. However, latency variation between a pacing signal and cardiac cycle portion typically indicates cardiac arrhythmia (tissue abnormality) and sudden cardiac electrophysiological changes or distortion. Hence a pacing heart beat success ratio is advantageously utilized as an indicator for early detection and characterization of patient cardiac arrhythmias, such as AF and acute myocardial ischemia, as follows, $$\text{Successful pacing beat ratio} = \frac{\text{Succesful\_heart\_beat\_number}}{\text{BPM\_of\_pacing}}$$

The successful heart beat number is derived by detection and capture of the number of successful heart beats in one time unit (e.g., one minute) and BPM (Beats per Minute) of pacing is a number set in an ICD or external pacer/stimulator as heart beat number per minute, for example.

Figure 4:
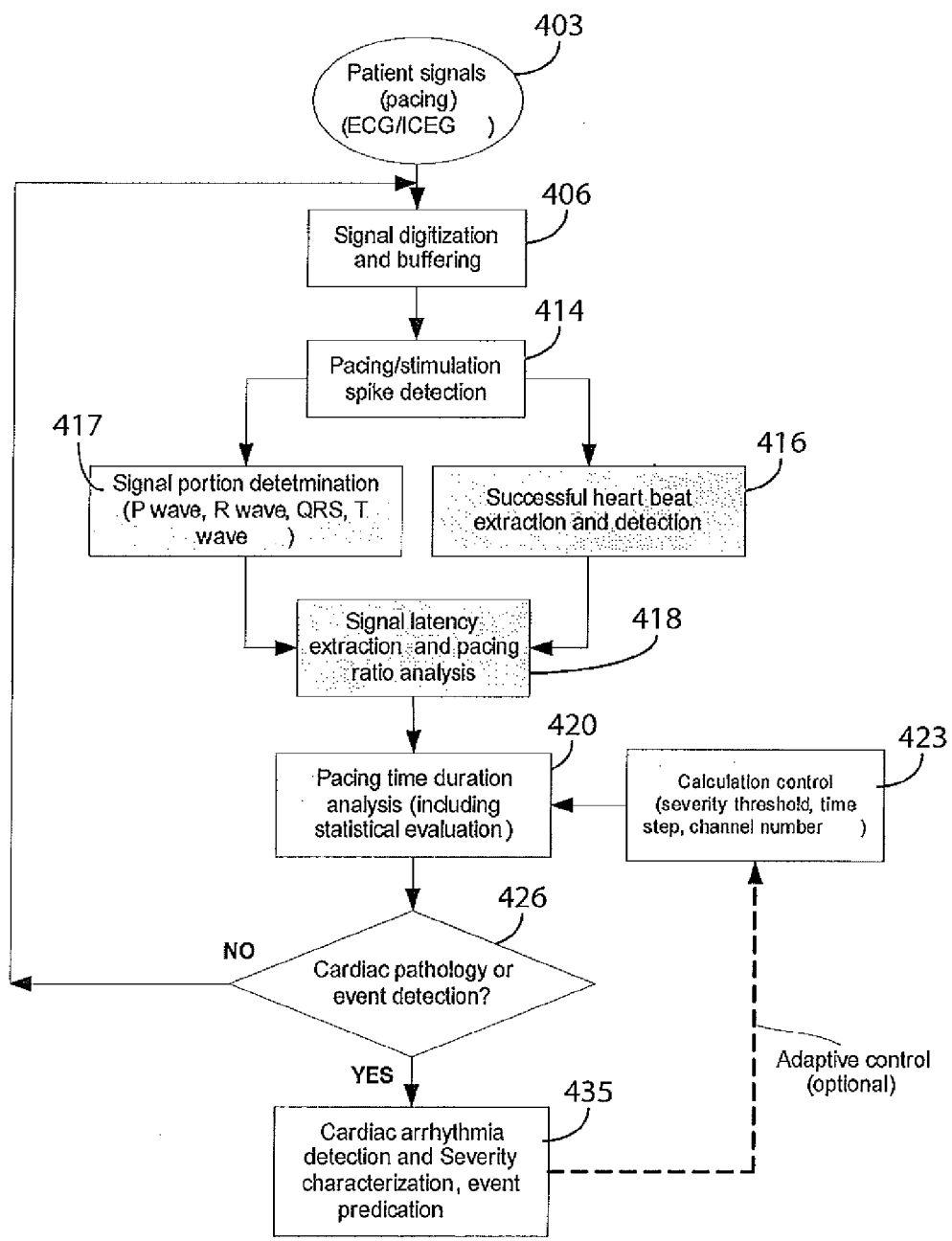
FIG. 4 shows a flowchart of a process for pacing signal calculation and analysis based cardiac arrhythmia and event detection and characterization, according to invention principles.

Pacing and stimulation signals generate different kinds of noise and artifacts in different frequency ranges and bandwidths. System 10 (FIG. 1) averages multiple heart beats to improve signal to noise ratio in latency analysis. FIG. 4 shows a flowchart of a process performed by system 10 for pacing signal calculation and analysis based cardiac arrhythmia and event detection and characterization. Interface 12 in step 403 acquires an electrical signal such as an ECG or ICEG electrophysiological signal indicating electrical activity of a patient heart over multiple heart beat cycles (or acquires electrophysiological signals from multiple channels of a multi-channel intra-cardiac (e.g., basket) catheter indicating electrical activity at multiple cardiac tissue sites) and acquires a pace signal indicating occurrence of a heart pace pulse applied to the heart. A heart pace or stimulation signal (e.g., of an ICD (intra-cardiac device), external stimulator) can be controlled and adjusted by a user for adjustment of heart beat rate, energy (voltage or current), pacing pulse width and pacing mode. Interface 12 in step 406 digitizes, buffers and filters the acquired signals and in step 414 detects a pulse (e.g., spike) in the acquired pace signal.

In step 416 signal processor 15 performs a successful heart beat detection and in step 417 signal processor 15 identifies different segments (QRS, ST, P wave, Q wave, R wave, S wave, ST segment, T wave, U wave segments, for example) of the filtered acquired signals. In step 418, signal processor 15 calculates Pace_Q, Pace_R, Pace_S and Pace_T parameters using the functions of the table of FIG. 3. Signal processor 15 also calculates a successful pacing beat ratio as previously described. Processor 15 in step 420 analyzes the calculated parameters by comparing the calculated parameters with predetermined thresholds identifying potentially abnormal results for the patient concerned. The thresholds are derived from a previous normal measurement of the patient or from a population of patients sharing similar demographic characteristics of the patient. Processor 15 also applies statistical analysis to the calculated parameters to look for potentially abnormal parameter values.

Processor 15 provides real time analysis and diagnosis of cardiac pathology (arrhythmia) and event detection and characterization, using predetermined (controllable and programmable) thresholds. Signal processor 15 employs mapping information, associating ranges of a calculated parameter value or values derived from the parameter value, with corresponding medical conditions (e.g., arrhythmias) in determining patient medical conditions, events and patient health status. If signal processor 15 and comparator 20 in step 426 determine a medical condition indicating cardiac impairment or another abnormality is identified, patient monitor 19 in step 435 generates an alert message identifying the medical condition and abnormality and communicates the message to a user. Processor 15 also determines the severity and location of the condition. Processor 15 (or a user in one embodiment) in step 423 adaptively adjusts calculation time step, the selected portions and ROI of a filtered signal analyzed and adjusts a threshold employed by comparator 20 to improve medical condition detection. If signal processor 15 and comparator 20 in step 426 does not identify a medical condition, the process is repeated from step 406.

Figure 5:
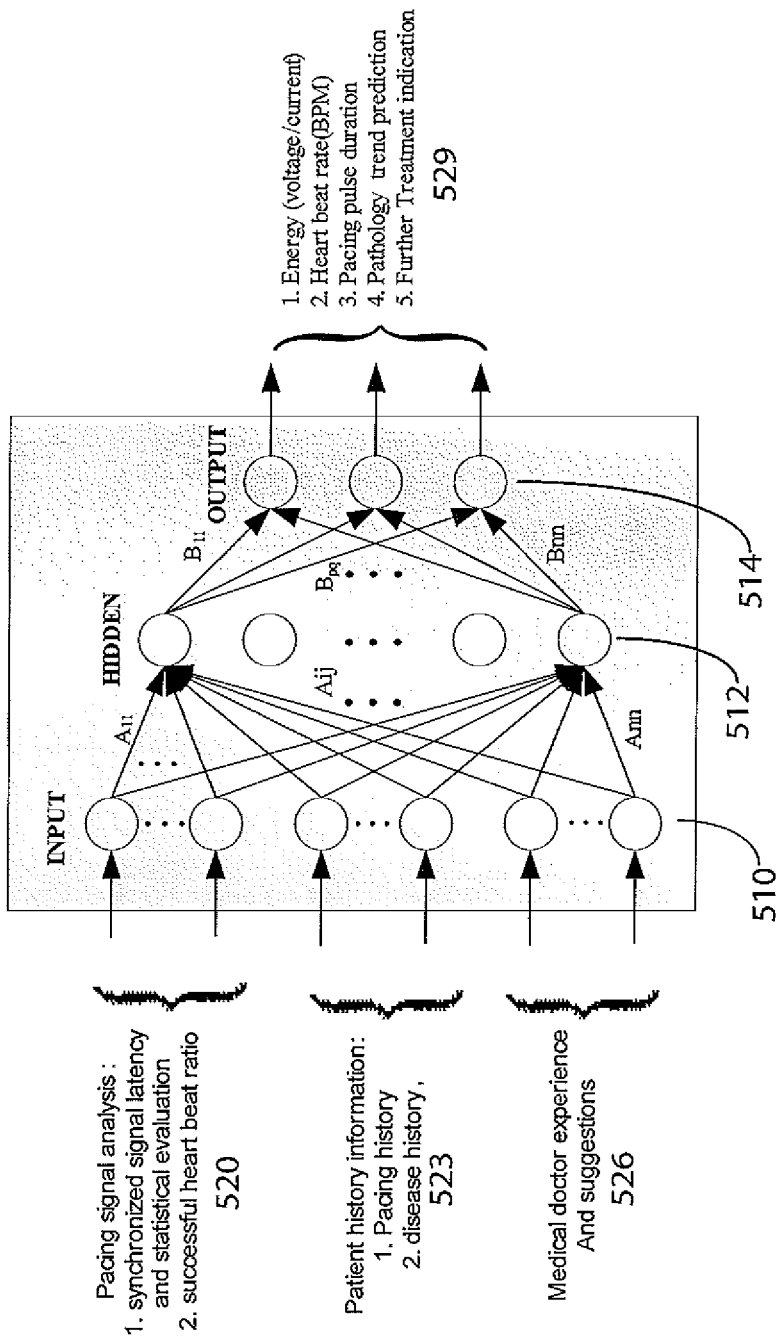
FIG. 5 shows an artificial neural network (ANN) used for automatic cardiac pacing and heart function analysis and detection, according to invention principles.

FIG. 5 shows an artificial neural network (ANN) system 507 used for automatic cardiac pacing and heart function analysis and detection. ANN unit 507 combines or maps one or more calculated Pace_Q, Pace_R, Pace_S and Pace_T parameters and successful pacing beat ratio 520, patient history 523 and physician suggestions and experience 526 (e.g., suggested control mode), to output parameters 529 which reduces the risk to patient heart tissue from over-pacing and tissue burning. Output parameters 529 include an energy (voltage and current) value, heart beat rate in (BPM), pacing pulse duration, a prediction of a trend in an identified condition and a treatment suggestion. ANN unit 507 structure comprises 3 layers, an input layer 510, hidden layer 512 and output layer 514. ANN unit $A_{ij}$ weights are applied between input layer 510 and hidden layer 512 components of the ANN computation and $B_{pq}$ weights are applied between hidden layer 512 and calculation components 514 of the ANN computation. The $A_{ij}$ weights and $B_{pq}$ weights are adaptively adjusted and tuned using a training data set. ANN unit 507 incorporates a self-learning function that processes signals 520, 523 and 526 to increase the accuracy of calculated results.

ANN unit 507 maps input signals 520, 523 and 526 to a candidate diagnosis or treatment suggestion 529 to localize a tissue impairment within an organ and determine time of occurrence within a heart cycle. ANN unit 507 also identifies arrhythmia type (e.g., AF, MI, VT, VF), severity of arrhythmia treatment and urgency level and is usable for automatic heart condition detection, diagnosis, warning and treatment. Further unit 507 performs statistical analysis to construct a threshold used to detect tissue impairment and diagnose and predict cardiac arrhythmia and pathology.

Following a training phase with a training data set, ANN unit 507 maps signals 520, 523 and 526 to data 529 indicating an Arrhythmia type, Arrhythmia severity, candidate treatment suggestions, localized tissue impairment information identifying the cardiac arrhythmia position, abnormal tissue area and focus of the disorder and irregularity, for example. The severity threshold of a pathology mapping decision may vary from person to person and is adjusted at the beginning of analysis. The system may be advantageously utilized in general patient monitoring and implantable cardiac devices for real time automatic analysis and detection of cardiac arrhythmias and abnormalities. ANN unit 507 is particularly useful in multi-channel pace signal latency and pattern analysis, for cross channel comparison and to further define arrhythmia type and location. Furthermore, ANN 507 employs different kinds of information, including a patient spike time stamp indicating time within an individual heart cycle of the spike that facilitates automatic control of pacing spike start time generation, using closed loop pacing spike generation based on pacing signal analysis, in addition to pacing and stimulation machine parameter control.

Pacing and stimulation (both internal and external to anatomy, such as provided by an ICD, pacemaker) automatic control and steering based on patient pacing signal analysis improves cardiac condition diagnosis and reduces physician workload and cost. For example, a pacemaker in a patient detects myocardial ischemia events and increases a heart beat rate 5 to 15 beats to prevent heart attack. The system 10 pacing signal analysis optimizes energy delivery from an ICD to patient heart tissue which saves battery energy and lowers risk to patients. In ICD patients, pacing signal analysis indicates the status of patient tissue which provides information for use in treating (or preventing) events and enables determination of reasonable (optimum) energy to be applied for AF (atrial fibrillation) at an optimum time. The synchronized pacing signal analysis and cardiac pathology analysis and event detection in one embodiment employs a multi-channel catheter, such as for an ICD application or a catheter application.

Figure 6:
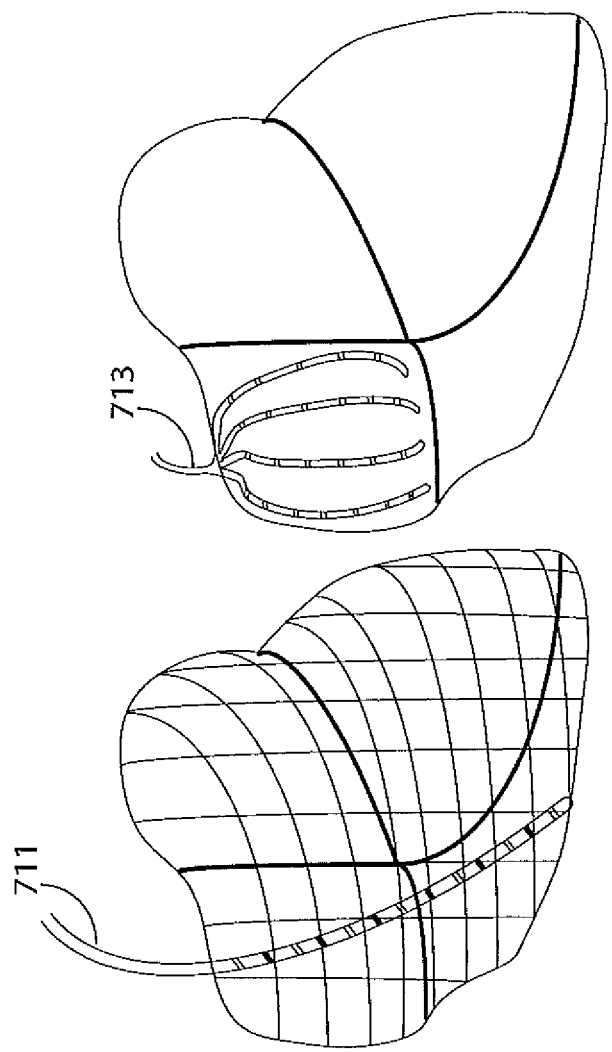
FIG. 6 illustrates an intra-cardiac catheter and EP (electrophysiological) signal based synchronized pacing signal analysis, according to invention principles.

FIG. 6 illustrates an intra-cardiac catheter and EP signal based synchronized pacing signal analysis in which a potential abnormal site is identified and characterized using heart pacing information mapping, such as Pace_R latency mapping derived using multi-lead or multi-channel heart signals. System 10 (FIG. 1) provides synchronized pacing signal analysis and mapping to medical conditions for use in monitoring cardiac internal excitation and a heart chamber, muscle and signal pathways. The system identifies location of abnormal tissue and arrhythmias and future deterioration by analyzing the excitation and pacing latency change and variation. This facilitates prevention of life threatening events. Catheter 711 is an EP catheter for multi-channel signal acquisition and comparison and pacing signal analysis. Catheter 713 is a basket catheter for multi-channel signal acquisition used for single heart chamber pacing diagnosis. The multi-channel pacing signal based cardiac status and function monitoring and analysis is used in 2-dimension and 3-dimension heart mapping (2D or 3D). Furthermore, the multi-dimensional pacing signal information mapping may be used in real time cardiac function diagnosis (signal latency versus time). Abnormal tissue location, potential abnormal pathways and arrhythmia severity are visually mapped to particular tissue regions by using multi-channel signal latency information mapping to associated heart location supporting user decision making and treatment selection.

Figure 7:
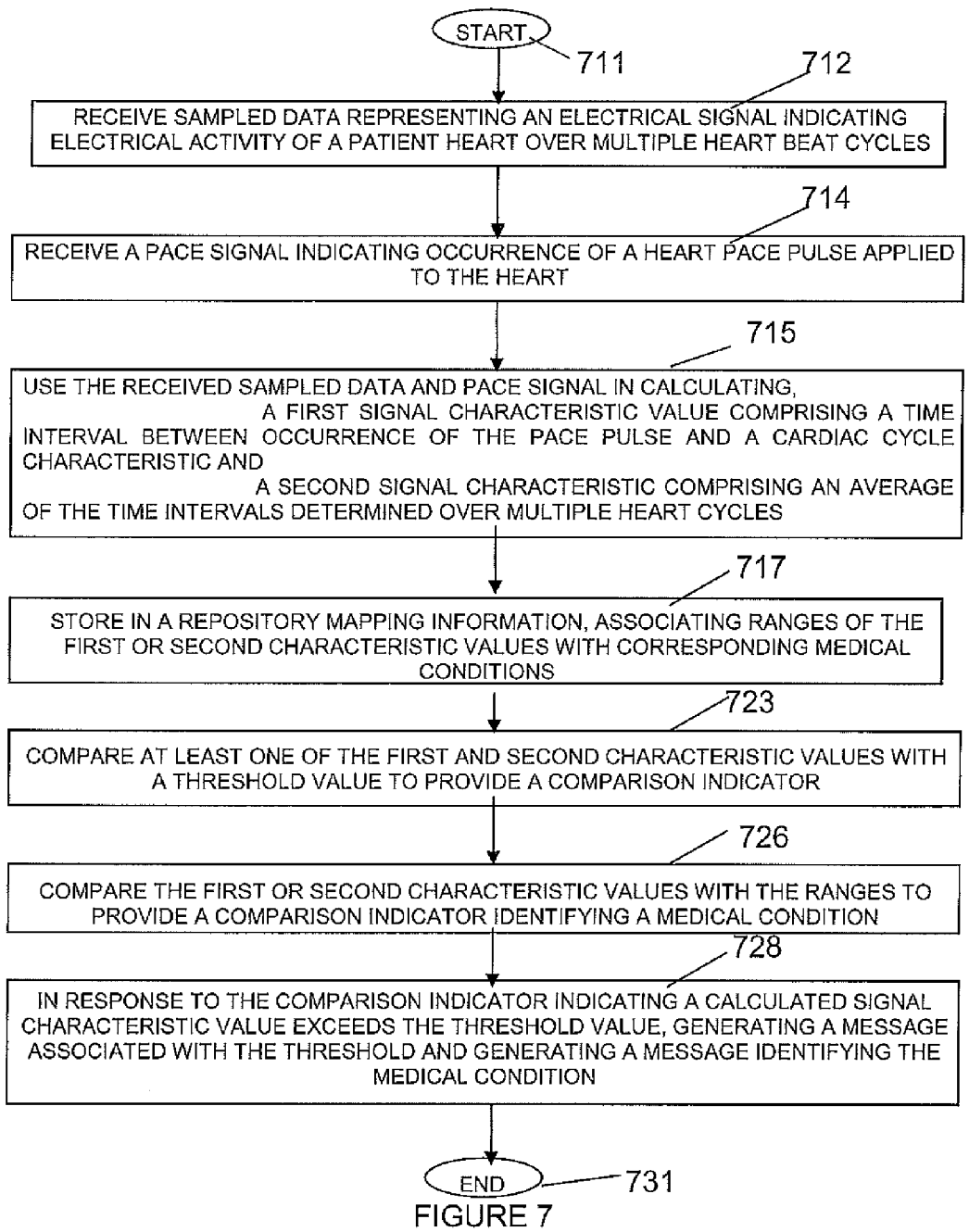
FIG. 7 shows a flowchart of a process used by a system for heart performance characterization and abnormality detection, according to invention principles.

FIG. 7 shows a flowchart of a process used by system 10 for heart performance characterization and abnormality detection. In step 712 following the start at step 711, interface 12 receives sampled data representing an electrical signal indicating electrical activity of a patient heart over multiple heart beat cycles and in step 714 receives a pace signal indicating occurrence of a heart pace pulse applied to the heart. Signal processor 15 in step 715 uses the received sampled data and pace signal in calculating, a first signal characteristic value comprising a time interval (within a single heart cycle) between occurrence of the pace pulse and a cardiac cycle characteristic and a second signal characteristic comprising an average of the time intervals determined over multiple heart cycles. The cardiac cycle characteristic comprises at least one of, (a) a Q wave point, (a) an R wave point, (c) an S wave point and (d) a T wave point.

Processor 15 calculates first signal characteristic values including values as follows. Signal processor 15 calculates the average of the time intervals determined over multiple heart cycles as, $$\frac{1}{N} \sum_{i \in N} \text{Pace\_X}(i)$$

where, Pace_X is the time interval between pacing spike and occurrence of the cardiac cycle characteristic and N is a calculation window size as there are N heart beats in a calculation window. Signal processor 15 calculates a standard deviation of the time intervals determined over multiple heart cycles as, $$\frac{1}{N-1} \sum_{i \in N-1} (\text{Pace\_X}(i) - \mu(\text{Pace\_X}))$$

where, Pace_X is the time interval between pacing spike and occurrence of the cardiac cycle characteristic and N is a calculation window size as there are N heart beats in a calculation window and μ(Pace_X) is the calculated average of the time intervals.

Processor 15 calculates a signal variability of the time intervals determined over multiple heart cycles as, $$\frac{\mu(Pace\_X)}{\phi(Pace\_X)} \text{ or its reciprocal,}$$

where, Pace_X is the time interval between pacing spike and occurrence of the cardiac cycle characteristic and N is a calculation window size as there are N heart beats in a calculation window and μ(Pace_X) is the calculated average of the time intervals and φ(Pace_X) is the standard deviation of the time intervals determined over multiple heart cycles. Processor 15 calculates a signal variation of the time intervals determined over multiple heart cycles as, $$\frac{\max(Pace\_X - \mu(Pace\_X))}{\mu(Pace\_X)} \text{ or its reciprocal,}$$

where, Pace_X is the time interval between pacing spike and occurrence of the cardiac cycle characteristic and N is a calculation window size as there are N heart beats in a calculation window and μ(Pace_X) is the calculated average of the time intervals.

In step 717, processor 15 stores mapping information in repository 17. The mapping information associates ranges of the first or second characteristic values with corresponding medical conditions. The predetermined mapping information associates ranges of the first or second characteristic values with particular patient demographic characteristics and with corresponding medical conditions and comparator 20 uses patient demographic data including at least one of, age weight, gender and height in comparing the ratio with the ranges and generating an alert message indicating a potential medical condition. Comparator 20 in step 723 compares at least one of the first and second characteristic values with a threshold value to provide a comparison indicator and in step 726 compares the first or second characteristic values with the ranges to determine a comparison indicator indicating whether at least one of the first and second characteristic values lies in a predetermined value range identifying a medical condition. The threshold value is derived from recorded electrical signal data for the patient concerned or for a population of patients that has similar demographic characteristics including at least two of, (a) age, (b) weight, (c) gender and (d) height, to those of the patient. Signal processor 15 dynamically adjusts the threshold value in response to a determined sensitivity of arrhythmia detection.

In addition, signal processor 15 identifies a number of successful heart beats identified over a time period and the comparator compares the number of successful heart beats with a corresponding number of pacing pulses provided in the time period to derive a heart performance indicator. In step 728, patient monitor 19 in response to the comparison indicator indicating a calculated signal characteristic value exceeds the threshold value, generates a message associated with the threshold and generates a message identifying the medical condition if the comparison indicator indicates a calculated signal characteristic value lies in a predetermined value range. Patient monitor 19 also generates an alert message, in response to a comparison indicator indicating, a calculated standard deviation value exceeds a predetermined threshold value, a calculated signal variability value exceeds a predetermined threshold value or a calculated signal variation value exceeds a predetermined threshold value. The process of FIG. 7 terminates at step 731.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-7 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system analyzes time duration between a pacing spike and an X wave portion (representing a cardiac signal portion, such as R wave, T wave) to identify cardiac pathology and events. Further, the processes and applications may, in alternative embodiments, be located on one or more (e.g., distributed) processing devices on a network linking the units of FIG. 1. Any of the functions and steps provided in FIGS. 1-7 may be implemented in hardware, software or a combination of both.

What is claimed is:

1. A system for heart performance characterization and abnormality detection, comprising:
    an interface for receiving sampled data representing an electrical signal indicating electrical activity of a patient heart over a plurality of heart beat cycles and for receiving a pace signal indicating occurrence of a heart pace pulse applied to the heart;
    a signal processor for using the received sampled data and pace signal in,
        determining a plurality of first signal characteristic values over a plurality of heart cycles, an individual first signal characteristic value comprising a time interval between occurrence of said pace pulse and a cardiac cycle characteristic and
        calculating a second signal characteristic comprising an average of said plurality of first signal characteristic values, said signal processor identifying a number of successful heart beats over a time period;
    a comparator configured to compare at least one of the first and second characteristic values with a threshold value to provide a comparison indicator and to compare said number of successful heart beats with a corresponding number of pacing pulses provided in the time period to derive a heart performance indicator; and
    a patient monitor for in response to said comparison indicator indicating a calculated signal characteristic value exceeds the threshold value, generating an alert message associated with the threshold.

2. A system according to claim 1, wherein
said time interval occurs within a single heart cycle.

3. A system according to claim 1, wherein
said comparator determines a comparison indicator indicating whether said at least one of the first and second characteristic values lies in a predetermined value range and
said patient monitor, in response to said comparison indicator indicating a calculated signal characteristic value lies in a predetermined value range, generates an alert message associated with the value range.

4. A system according to claim 1, wherein
said cardiac cycle characteristic comprises at least one of, (a) a Q wave point, (a) an R wave point, (c) an S wave point and (d) a T wave point.

5. A system according to claim 1, wherein
said threshold value is derived from recorded electrical signal data for said patient.

6. A system according to claim 1, wherein
said threshold value is derived from recorded electrical signal data for a population of patients.

7. A system according to claim 6, wherein
said population of patients has similar demographic characteristics including at least two of, (a) age, (b) weight, (c) gender and (d) height, to those of said patient.

8. A system according to claim 1, wherein
said signal processor dynamically adjusts said threshold value in response to a determined sensitivity of arrhythmia detection.

9. A system according to claim 1, wherein
said signal processor calculates said average of said first signal characteristic values determined over a plurality of heart cycles as, $$\frac{1}{N} \sum_{i \in N} \text{Pace\_X}(i)$$

where, Pace_X is the time interval between pacing spike and occurrence of said cardiac cycle characteristic and N is a calculation window size as there are N heart beats in a calculation window.

10. A system according to claim 1, wherein
said signal processor calculates a standard deviation of said first signal characteristic values determined over a plurality of heart cycles and
said patient monitor, in response to a comparison indicator indicating a calculated standard deviation value exceeds a predetermined threshold value, generates an alert message.

11. A system according to claim 10, wherein
said signal processor calculates a standard deviation of said first signal characteristic values determined over a plurality of heart cycles as, $$\frac{1}{N-1} \sum_{i \in N-1} (\text{Pace\_X}(i) - \mu(\text{Pace\_X}))$$

where, Pace_X is the time interval between pacing spike and occurrence of said cardiac cycle characteristic and N is a calculation window size as there are N heart beats in a calculation window and μ(Pace_X) is the calculated average of said first signal characteristic values.

12. A system according to claim 1, wherein
said signal processor calculates a signal variability of said first signal characteristic values determined over a plurality of heart cycles and
said patient monitor, in response to a comparison indicator indicating a calculated signal variability value exceeds a predetermined threshold value, generates an alert message.

13. A system according to claim 12, wherein
said signal processor calculates a signal variability of said first signal characteristic values determined over a plurality of heart cycles as, $$\frac{\mu(\text{Pace\_X})}{\phi(\text{Pace\_X})} \text{ or its reciprocal,}$$

where, Pace_X is the time interval between pacing spike and occurrence of said cardiac cycle characteristic and N is a calculation window size as there are N heart beats in a calculation window and μ(Pace_X) is the calculated average of said first signal characteristic values and ϕ(Pace_X) is the standard deviation of said first signal characteristic values determined over a plurality of heart cycles.

14. A system according to claim 1, wherein
said signal processor calculates a signal variation of said first signal characteristic values determined over a plurality of heart cycles and
said patient monitor, in response to a comparison indicator indicating a calculated signal variation value exceeds a predetermined threshold value, generates an alert message.

15. A system according to claim 14, wherein
said signal processor calculates a signal variation of said first signal characteristic values determined over a plurality of heart cycles as, $$\frac{\max(\text{Pace\_X} - \mu(\text{Pace\_X}))}{\mu(\text{Pace\_X})} \text{ or its reciprocal,}$$

where, Pace_X is the time interval between pacing spike and occurrence of said cardiac cycle characteristic and N is a calculation window size as there are N heart beats in a calculation window and μ(Pace_X) is the calculated average of said first signal characteristic values.

16. A system according to claim 1, wherein
said threshold value is derived from recorded electrical signal data for a population of patients and said signal processor dynamically adjusts said threshold value in response to a determined sensitivity of arrhythmia detection.

17. A system according to claim 1, including
a repository of predetermined mapping information, associating ranges of the first or second characteristic values with corresponding medical conditions and
said comparator compares the first or second characteristic values with said ranges to provide a comparison indicator identifying a medical condition and
said patient monitor generates an alert message identifying said medical condition.

18. A system according to claim 17, wherein
said predetermined mapping information associates ranges of the first or second characteristic values with particular patient demographic characteristics and with corresponding medical conditions and said system uses patient demographic data including at least one of, age weight, gender and height in comparing the ratio with said ranges and generating an alert message indicating a potential medical condition.

19. A system for heart performance characterization and abnormality detection, comprising:
an interface for receiving sampled data representing an electrical signal indicating electrical activity of a patient heart over a plurality of heart beat cycles and for receiving a pace signal indicating occurrence of a heart pace pulse applied to the heart;
a signal processor for using the received sampled data and pace signal in,
determining a plurality of first signal characteristic values over a plurality of heart cycles, an individual first signal characteristic value comprising a time interval between occurrence of said pace pulse and a cardiac cycle characteristic and
calculating a second signal characteristic comprising an average of said plurality of first signal characteristic values, said signal processor identifying a number of successful heart beats over a time period;
a repository of mapping information, associating ranges of the first or second characteristic values with corresponding medical conditions;
a comparator configured to compare at least one of the first and second characteristic values with a threshold value to provide a comparison indicator and to compare the first or second characteristic values with said ranges to provide a comparison indicator identifying a medical condition and to compare said number of successful heart beats with a corresponding number of pacing pulses provided in the time period to derive a heart performance indicator; and
a patient monitor for in response to said comparison indicator indicating a calculated signal characteristic value exceeds the threshold value, generating a message associated with the threshold and generating a message identifying said medical condition.

20. A method for heart performance characterization and abnormality detection, comprising the activities of:
receiving sampled data representing an electrical signal indicating electrical activity of a patient heart over a plurality of heart beat cycles;
receiving a pace signal indicating occurrence of a heart pace pulse applied to the heart;
using the received sampled data and pace signal in,
determining a plurality of first signal characteristic values over a plurality of heart cycles, an individual first signal characteristic value comprising a time interval between occurrence of said pace pulse and a cardiac cycle characteristic,
calculating a second signal characteristic comprising an average of said plurality of first signal characteristic values and
identifying a number of successful heart beats over a time period and
comparing said number of successful heart beats with a corresponding number of pacing pulses provided in the time period to derive a heart performance indicator;
comparing at least one of the first and second characteristic values with a threshold value to provide a comparison indicator; and
in response to said comparison indicator indicating a calculated signal characteristic value exceeds the threshold value, generating an alert message associated with the threshold.

* * * * *